United States Patent [19]

Cantrell

[11] Patent Number: 4,973,772
[45] Date of Patent: * Nov. 27, 1990

[54] CATALYTIC METHOD FOR PRODUCING FLUOROARMATIC COMPOUNDS USING SUBSTITUTED PYRIDINIUM SALTS

[75] Inventor: Gary L. Cantrell, Belleville, Ill.

[73] Assignee: Mallinckrodt, Inc., St. Louis, Mo.

[*] Notice: The portion of the term of this patent subsequent to May 22, 2007 has been disclaimed.

[21] Appl. No.: 146,257

[22] Filed: Feb. 7, 1987

[51] Int. Cl.$^5$ ............................................. C07C 205/87
[52] U.S. Cl. .................................. 568/937; 546/304; 548/486; 568/938
[58] Field of Search ...................... 568/937, 938, 937; 546/304; 548/486

[56] References Cited

U.S. PATENT DOCUMENTS

| | | |
|---|---|---|
| 3,064,058 | 11/1962 | Duesel et al. |
| 3,240,824 | 3/1966 | Boudakian et al. |
| 3,992,432 | 11/1976 | Napier et al. |
| 4,069,262 | 1/1978 | Kunz . |
| 4,140,719 | 2/1979 | Tull et al. |
| 4,164,517 | 8/1979 | Fuller . |
| 4,226,811 | 10/1980 | Oeser et al. |
| 4,229,365 | 10/1980 | Oeser et al. |
| 4,252,739 | 2/1981 | Fayter, Jr. et al. |
| 4,287,374 | 1/1981 | North . |
| 4,418,229 | 11/1983 | White . |
| 4,460,778 | 7/1984 | Brunelle . |
| 4,513,141 | 4/1985 | Brunelle et al. |
| 4,595,760 | 6/1986 | Brunelle . |
| 4,605,745 | 8/1986 | Brunelle et al. |

FOREIGN PATENT DOCUMENTS 7038726 8/1980 Japan .
1469700 4/1977 United Kingdom .
2042507 10/1978 United Kingdom .
2058067 4/1981 United Kingdom .

OTHER PUBLICATIONS

Brunelle et al., "N-Alkyl-4-(N,N'-Dialkylamino) Pyridinium Salts: Thermally Stable Transfer Catalysts for Nucleophilic Aromatic Displacement"-Tetrahedron Letters, vol. 25, No. 32, pp. 3383-3386, 1984.

Chem Abstracts, vol. 97, 55468s (1982).

T. Tamaka et al., Chemistry Letters, pp. 1259-1262, 1976.

Stanks, "Selecting a Phase Transfer Catalyst" Chemtech, Feb. 1980, pp. 110-117.

G. C. Finger et al., J. Am. Chem Soc., 78, 6034-6037, (1956).

Primary Examiner—Robert L. Stoll
Assistant Examiner—Valarie D. Fee
Attorney, Agent, or Firm—Roy J. Klostermann

[57] ABSTRACT

A process is disclosed for preparing fluoroaromatic compounds (such as fluoronitrobenzene compounds) by reaction of corresponding chloroacromatic compounds (such as chloronitrobenzene compounds) with alkali metal fluoride salts in the presence of alkyldiorganoaminopyridinium salts as phase transfer catalysts. A tertiary carbon atom is directly attached to the alkyl carbon atom which is directly attached to the ring nitrogen atom. A preferred catalyst is N-neopentyl-4-(4'-methylpiperidinyl)pyridinium chloride.

11 Claims, No Drawings

CATALYTIC METHOD FOR PRODUCING FLUOROARMATIC COMPOUNDS USING SUBSTITUTED PYRIDINIUM SALTS

BACKGROUND OF THE INVENTION

This application is a continuation-in-part of application Ser. No. 816,478, filed Jan. 6, 1986 now abandoned, The present invention relates to N-secondary-alkyldiorganoaminopyridinium salts useful as phase transfer catalysts for facilitating preparation of fluoroaromatic compounds (such as fluoronitrobenzene compounds.)

Fluoronitrobenzene compounds such as 2-fluoronitrobenzene, 4-fluoronitrobenzene, and 2,4-difluoronitrobenzene, are useful as intermediates for the synthesis of various herbicidal compounds, dyes, and the like. Such compounds have been prepared from corresponding chloronitrobenzene compounds by so-called halogen exchange reactions, illustrated as follows:

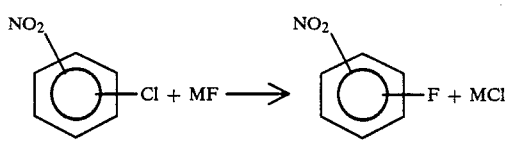

wherein MF represents an alkali metal fluoride salt. The reaction is generally conducted in an aprotic, polar, organic solvent. such as dimethylsulfoxide, dimethylformamide, tetramethylenesulfone (sulfolane), and the like.

Alkali metal fluoride salts are not soluble in such solvents. Therefore, the reaction mixtures usually contain two phases, i.e., solid and liquid phases or two immiscible liquid phases, Finger, et al., *J. Am. Chem Soc.*, 78, 6034 (1956) and Duesel, et al., U.S. Pat. No. 3,064,058 (1962), describe the reaction of chloronitrobenzene compounds with finely-divided, solid potassium fluoride in aprotic polar solvents to produce corresponding fluoronitrobenzene compounds. Boudakian, et al., U.S. Pat. No. 3,240,824 (1966), describe the reaction of o-chloronitrobenzene with solid potassium fluoride at elevated temperatures, without any solvent or diluents, to produce o-fluoronitrobenzene. Napier and Starks, U.S. Pat. No. 3,992,432 (1976), describe a reaction involving two liquid phases. In the Napier and Starks reaction, the inorganic fluoride salt is dissolved in an aqueous phase, and the chloronitrobenzene compound is dissolved in a water-immiscible, organic phase. The reaction is catalyzed by a quaternary salt, which reportedly transfers ions across the phase interface.

Use of quaternary salt phase-transfer catalysts in solid-liquid, two phase reactions also has been known. For instance, Kunz, U.S. Pat. No. 4,069,262 (1978), describes the production of 2-fluoronitrobenzene by reacting 2-chloronitrobenzene with ultrafine particulate potassium fluoride in tetramethylenesulfone solvent using a macrocyclic ether (crown ether) or a quaternary ammonium halide (such as tetrabutylammonium chloride, benzyltrimethylammonium chloride, benzyltrimethylammonium fluoride or benzyltriethylammonium chloride) as the catalyst.

Tull, et al., U.S. Pat. No. 4,140,719 (1979), describes the production of 2,4-difluoro-5-chloronitrobenzene by reacting 2,4,5-trichloronitrobenzene with a solid fluorinating agent selected from NaF, KF, CsF, and $C_{1-4}$alkyl quaternary ammonium fluoride, and mixtures thereof under substantially anhydrous conditions in the presence of a quaternary compound solid-liquid phase transfer catalyst. The liquid phase comprises an organic solvent in which the trichloro compound is soluble and the fluorinating agent is essentially insoluble.

Starks, "Selecting a Phase Transfer Catalyst," *Chemtech* (February 1980), pages 110-117, describes patterns that purportedly enable prediction of catalysts for anion transfer from aqueous or solid inorganic phases to organic phases.

North, U.S. Pat. No. 4,287,374 (1981) discloses a process for the production of a monofluoronitrobenzene in which a monochloronitrobenzene is heated with an alkali metal fluoride and a phase transfer catalyst at a temperature of no more than 200° C., preferably 125°-170° C., especially 140°-150° C. North discloses, as examples of such catalysts which may be used, long chain alkylammonium halides.

In general, halide-exchange reactions for preparing fluoronitrobenzene compounds by reacting chloronitrobenzene compounds with fluoride salts in aprotic, polar organic solvents in the presence of quaternary ammonium salt phase-transfer catalysts proceed at faster rates when conducted at elevated temperature relative to rates obtainable at lower temperature. However, quaternary ammonium phase-transfer catalysts employed in heretofore known methods are less stable at higher temperature and have been found to decompose or lose their catalytic activity at elevated reaction temperatures. Moreover, U.S. Pat. No. 4,418,229 (to White), incorporated herein by reference, discloses that lower molecular weight catalysts, i.e., those having a total number of carbon atoms less than about 16, are less stable under the conditions (including elevated temperature) of the method of the invention disclosed therein than the therein preferred catalysts of higher molecular weight having about 6 or more carbon atoms.

The above cited White patent discloses the finding that in the conversion of chloronitrobenzene ("CNB") compounds to corresponding fluoronitrobenzene ("FNB") compounds using a quaternary ammonium salt phase-transfer catalyst at elevated temperatures, a high level of catalytic activity can be maintained by adding the catalyst to the reaction mixture incrementally during the course of the reaction However, there remains a substantial need in the art for new and improved processes for preparing fluoroaromatic compounds such as fluoronitrobenzenes. The present invention substantially fulfills such need.

DESCRIPTION OF THE INVENTION

Generally stated, the present invention provides an improved method for producing fluoroaromatic compounds (e.g. fluoronitrobenzene compounds) which includes reacting a chloroaromatic compound (e.g. a chloronitrobenzene compound) with a fluoride salt in a substantially anhydrous reaction mixture under halide-exchange conditions in the presence of a catalyzing amount of a phase-transfer catalyst, wherein the improvement comprises using an alkyldiorganoaminopyridinium salt (hereinafter sometimes referred to as PYR salt) as the phase-transfer catalyst.

The use of PYR salt as the catalyst allows use of an elevated reaction temperature with substantial freedom from inactivation of the catalyst, resulting in good reaction rates and yields The improved method is also effective for the conservation of catalyst at such elevated temperatures.

Alkyldiorganoaminopyridinium salts (or simply, PYR salts) which can be employed as the phase-transfer catalyst in the improved method are represented by the formula

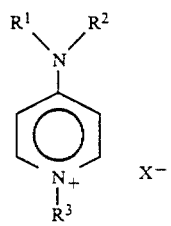 (1)

where:

R$^1$ and R$^2$ are monovalent or divalent organo radicals independently selected from substituted and unsubstituted hydrocarbon radicals having from 1 to 13 carbon atoms and divalent alkylene radicals which together can be a part of a cyclic structure forming a ring having from 4 to 8 carbon atoms;

R$^3$ is a monovalent organo radical represented by the formula $$-CH_2-\underset{\underset{R^6}{|}}{\overset{\overset{R^4}{|}}{C}}-R^5 \qquad (2)$$

where R$^4$, R$^5$ and R$^6$ are independently selected alkyl radicals having from 1 to about 8 carbon atoms, subject to the proviso that the total number of carbon atoms in R$^3$ is not more than about 20; and X$^-$ is an anion selected from the group consisting of fluoride, bromide and chloride.

DETAILED DESCRIPTION OF THE INVENTION AND OF THE MANNER AND PROCESS OF MAKING AND USING IT

Included within the N-alkyl-diorganoaminopyridinium salts of formula (1) are for example (i) N-neopentyl-4-(N',N'-di-n-butylamino)pyridinium chloride which has the formula

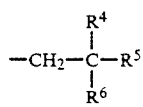

(ii) N-neopentyl-4-(N',N'-di-n-hexylamino)-pyridinium chloride which has the formula

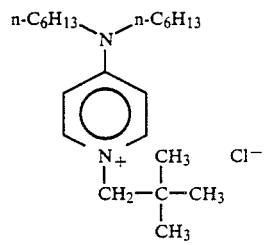

(iii) N-neopentyl-4-(4'-methylpiperidinyl)pyridinium chloride which has the formula

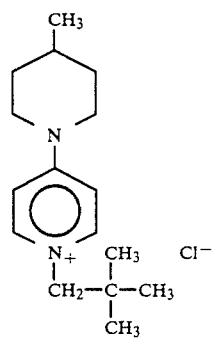

The N-alkyldiorganoaminopyridinium salts of formula (1) can be made by alkylating diorganoaminopyridines which can be made by reacting 4-hydroxypyridine with phosphorous pentoxide and a diorganoamine at 200° C. to 300° C., for example, 250° C. as shown by the following equation:

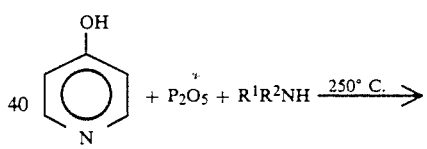

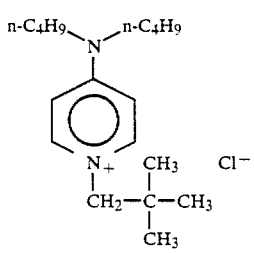

where R$^1$ and R$^2$ are as defined above.

The alkylation of the above diorganoaminopyridines can be achieved in a straight forward manner utilizing such reagents as neopentylbromide, 2,2-dimethylbutylbromide, 2,2-dimethylhexylbromide and the like at ambient temperatures in an inert organic solvent, for example, chloroform or toluene. Reaction with such alkyl compounds, as well as the corresponding tosylate or mesylate can be facilitated by using higher temperatures such as refluxing toluene, or temperatures up to about 150° C.

A preferred salt for use as a phase transfer catalyst in preparing fluoroaromatic (e.g. FNB) compounds from corresponding chloroaromatic (e.g. CNB) compounds is the salt of formula (iii). The best salt contemplated for such use is the salt of formula (i).

The halide-exchange conditions generally include elevated reaction temperatures, which are high enough to provide sufficient energy of activation for the reaction Although such reaction temperatures might cause some catalyst inactivation, the temperature is preferably not so high as to cause rapid decay of catalytic activity or substantial decomposition of the reactants, the products, or the solvent Although the reaction temperature may vary, depending upon the particular catalyst, solvent, and reactants used, generally it may be, for example, from about 120° C. to about 220° C., preferably from about 160° C. to about 215° C., and more preferably from about 205° C. to about 215° C.

Those skilled in the art will appreciate that a variety of equipment and techniques may be utilized in the method of the present invention, and the invention is not limited to any particular equipment or technique. The method is generally conducted by charging the reactants, solvent and PYR salt catalyst into a reaction vessel which is equipped with agitating and heating means. Advantageously, the entire amount of the reactants, solvent and PYR salt catalyst to be employed can be added initially. The reaction vessel may also advantageously include a reflux condenser or other means of recovering solvent vapors and means for blanketing the reaction mixture with a dry inert gas, e.g., nitrogen. The reaction mixture is heated to the desired reaction temperature and agitated.

The halide-exchange reaction conditions employed in the present invention advantageously include substantially anhydrous reaction conditions. The presence of water in the reaction can diminish yields and result in undesirable by-products various techniques may be used for dehydrating the reactants and solvent, such as vacuum drying, azeotropic distillation, chemical drying and the like Azeotropic distillation, for example with benzene, can be used for drying all of the reactants and solvents; however, any convenient and operable technique may be employed. Due to the deleterious effect of water, the reaction mixture is preferably substantially devoid of water. Small amounts of water may be tolerated: however, a corresponding reduction in yield is generally experienced Advantageously, the concentration of water in the reaction mixture is below about 5 wt. % and is preferably below about ]wt. %, based on the weight of the reaction mixture.

The solvent for the catalyst, chloroaromatic (e.g. CNB) compound, and fluoroaromatic (e.g. FNB) compound is an aprotic, polar, organic solvent, which preferably has a relatively high boiling point, e g., a boiling point above about 190° C. Lower boiling solvents may be used; however, pressure reactors may be required for their containment. Solvents having boiling points below a desired reaction temperature may be employed by conducting the reaction under superatmospheric pressure in such reactors Examples of reaction solvents include dimethylsulfoxide, sulfolane, bis(2-methoxyethyl)ether, bis 2-(2-methoxyethoxy) ethyl ether, hexamethylphosphoramide, N-methylpyrolidinone, and dimethylformamide. Dimethylformamide and sulfolane are preferred solvents. Sulfolane is most preferred from the standpoint of commercial attractiveness.

The phase-transfer catalyst employed in the present method is soluble in the reaction solvent in an amount sufficient to catalyze the reaction. The PYR salt may be employed in any catalyzing amount, i.e., in any amount effective for catalyzing the conversion of the chloroaromatic (e.g. CNB) compound to the corresponding fluoroaromatic (e.g., FNB) compound. In general, the amount may correspond, for example, to a molar ratio of PYR salt to chloroaromatic (e.g. CNB) compound of from about 0.005:1 to about 0.5:!, preferably from about 0.04:1 to about 0.15:1, most preferably about 0.08:1. In general, amounts of PYR salt corresponding to molar ratios of less than about 0.005:1 may not provide sufficient catalytic activity, while amounts corresponding to molar ratios of more than 0.5:1 may result in insufficient additional benefit to justify the additional cost. As indicated above, the entire amount of PYR salt to be used is preferably added initially. However, if desired, a portion may be added initially with incremental addition of the remainder during the course of the reaction Incremental addition may be, for example, substantially in accordance with the invention disclosed in the above-cited White patent.

The fluoride ion is provided by an alkali metal fluoride salt which is generally present in an amount at least substantially stoichiometric to the chloroaromatic (e.g. CNB)reactant. Preferred fluoride salts are potassium fluoride, rubidium fluoride, and cesium fluoride, and potassium fluoride is particularly preferred. The fluoride salt is advantageously finely-divided, to provide a greater superficial surface area which is accessible to the catalyst and the chloroaromatic (e.g. CNB) compound Preferred concentrations of the fluoride salt range from about 1 to about 2 times the stoichiometric amount, most preferably from about 1.2 to about 1.6 times such amount. For example, in a method for producing a monofluoronitrobenzene compound, a preferred molar ratio of fluoride salt to chloronitrobenzene compound is about 1.5:1. Lower concentrations of fluoride salts can result in diminished reaction rates, and, although higher concentrations can be· used no appreciable benefit is generally realized therefrom.

In the chloronitrobenzene compound used as a starting material in the present invention, the relative positions of the nitro and chloro substituents, and the presence of other substituents on the ring can affect the reactivity of the starting compound. Generally, halogen exchange reactions involve compounds in which the chloride is in the ortho or para position with respect to the nitro group, and reactivity may increase when other electron-withdrawing groups are present on the ring. Compounds having chloro substituents in the meta as well as ortho and/or para positions may be used as starting materials, but usually only the chloro groups in the ortho and para positions will undergo halogen exchange. Accordingly, the method of this invention may be used for example for the synthesis of compounds such as 2-fluoronitrobenzene, 2-fluoro-3-chloronitrobenzene, 4-fluoronitrobenzene, 2,4-difluoronitrobenzene, 5-chloro-2,4-difluoronitrobenzene, and the like, from corresponding chloronitrobenzene compounds. The present method is particularly useful for the preparation of 4-fluoronitrobenzene from 4-chloronitrobenzene and 2-fluoronitrobenzene from 2-chloronitrobenzene.

The reaction is generally allowed to proceed until substantially all the chloroaromatic (e.g. CNB) compound has been converted to the corresponding fluoroaromatic (e.g. FNB) invention may be used for example for the synthesis of compound. A reaction time of from about 10 minutes to about 20 hours may typically be used, and the reaction will often be substantially complete after about 1 to about 6 hours. After the reaction is completed, the product can be recovered by any suitable procedure, such as extraction, distillation, steam distillation and the like. For some purposes, the purity of the crude reaction product, recovered as an organic phase after addition of water to the reaction mixture, will be satisfactory.

The method of this invention has been found to produce fluoronitrobenzene compounds in good yields with little formation of by-products.

Although the above description of the improved halide-exchange process of this invention has been given principally with reference to effecting conversion of chloroaromatic (e.g. CNB) compounds to corresponding fluoroaromatic (e.g. FNB)compounds in the presence of a solvent, the halide-exchange reaction can be carried out as a neat (i.e., solventless) reaction with the chloroaromatic (e.g. CNB) compound in "the melt" (i.e. in a molten state).

Chloroaromatic compounds suitable for use in the process of this invention include an aromatic ring, at least one chlorine atom as a substituent on the aromatic ring and at least one activating substituent located in an activating position on the ring (or facilitating the desired nucleophilic substitution, i.e., exchange of fluorine for the chlorine. The activating substituent is an electron-withdrawinq agent, including for example: nitro; cyano; trifluoromethyl; chlorocarbonyl; fluorocarbonyl; phenylcarbonyl wherein the phenyl moiety is unsubstituted or substituted with a substituent other than agents which are at least moderately strong electron-releasing agents (i.e., substituted with, for example, chloro, nitro, cyano, trifluoromethyl, and linear or branched alkyl groups, preferably having from 1 to about 12 carbon atoms); phenylsulfonyl wherein the phenyl moiety is unsubstituted or substituted with a substituent other than agents which are at least moderately strong electron-releasing agents (i.e., substituted with, for example, chloro, nitro, cyano, trifluoromethyl and linear or branched alkyl groups, preferably having from 1 to about 12 carbon atoms); and a combination of three, four or five additional chlorine atoms. In general, the chlorine atoms to be exchanged are in the ortho and/or para positions relative to the activating agent.

The aromatic ring may be, for example, a benzene ring or a pyridine ring.

Suitable chloroaromatic compounds for use in this invention include, for example:
(a) 2-chlorobenzonitrile
(b) 4-chlorobenzonitrile
(c) 2-chlorobenzoyl chloride
(d) 4-chlorobenzoyl chloride
(e) 2-chlorobenzoyl fluoride
(f) 4-chlorobenzoyl fluoride
(g) 2-chloro-benzotrifluoride
(h) 4-chloro-benzotrifluoride
(i) tetrachlorobenzene
(j) pentachlorobenzene
(k) hexachlorobenzene
(l) (4,4'-dichloro-)diphenylsulfone
(m) 4,4'-dichlorobenzophenone
(n) 3-chloro-phthalic anhydride
(o) 4-chloro-phthalic anhydride
(p) 3-chloro-phthaloyl dichloride
(q) 4-chloro-phthaloyl dichloride
(r) 1,4-dichloroanthracene-9,10-dione
(s) 3-chloro-4-(trifluoromethyl)pyridine
(t) 3-chloro-4-cyanopyridine
(u) 3-chloro-4-nitropyridine.
(v) 2-chloronitrobenzene
(w) 2,3-dichloronitrobenzene
(x) 4-chloronitrobenzene
(y) 2,4-dichloronitrobenzene and
(z) 2,4,5-trichloronitrobenzene.

The fluoroaromatic compounds resulting from carrying out the process of this invention using the illustrative chloroaromatic compounds (a) through (z) above are set forth below, followed by utilities for such resulting compounds:
(a) 2-fluorobenzonitrile
(b) 4-fluorobenzonitrile
(c) 2-fluorobenzoyl chloride
(d) 4-fluorobenzoyl chloride
(e) 2-fluorobenzoyl fluoride
(f) 4-fluorobenzoyl fluoride
(g) 2-fluorobenzotrifluoride
(h) 4-fluorobenzotrifluoride
(i) tetrafluorobenzene
(j) pentafluorobenzene
(k) hexafluorobenzene
(l) (4,4'-difluoro-)diphenylsulfone
(m) 4,4'-difluorobenzophenone
(n) 3-fluoro-phthalic anhydride
(o) 4-fluoro-phthalic anhydride
(p) 3-fluoro-phthaloyl dichloride
(q) 4-fluoro-phthaloyl dichloride
(r) 1,4-difluoroanthracene-9,10-dione
(s) 3-fluoro-4-(trifluoromethyl)pyridine
(t) 3-fluoro-4-cyanopyridine
(u) 3-fluoro-4-nitropyridine.
(v) 2-fluoronitrobenzene
(w) 2-fluoro-3-chloronitrobenzene
(x) 4-fluoronitrobenzene
(y) 2,4-difluoronitrobenzene and
(z) 5-chloro-2,4-difluoronitrobenzene.

Fluoroaromatic compounds (a) through (f) can be hydrolyzed to the corresponding fluorobenzoic acids, which are useful as intermediates for preparing herbicides and liquid crystals. The trifluoromethyl products (g) and (h) are useful as intermediates for preparing herbicides and medicinal agents such as flumetramide. The polyfluorobenzene compounds (i), (j) and (k) are useful as intermediates for preparing plant growth regulators. The fluorosulfone compound (l) is useful as a crosslinking agent and as a monomer which can be polymerized to provide engineering plastics. The fluoroketone (m) is useful as a monomer which can be polymerized to provide engineering plastics. The fluoroanhydrides (n) and (o) and the corresponding acid chlorides (p) and (q) are useful for esterifying with polyols to prepare fluorinated polyesters which are useful as wear-resistant fibers. The fluorinated anthracene dione (r) can be converted by well known methods to 1,4-bis[-(aminoalkyl)amino]-anthracene-9,10-diones which are useful as antineoplastics. The fluoropyridine compounds (s), (t) and (u) and the fluoronitrobenzene compounds (v), (w), (x), (y) and (z) are useful as intermediates for making herbicides and dyes.

Practice of this invention is further illustrated by the following non-limiting examples All parts, percents and other amounts throughout this disclosure are by weight unless otherwise indicated.

EXAMPLE I

Neopentyl alcohol (16 5 grams) was dissolved in 75 ml of acetonitrile. Methane sulfonyl chloride (21.4 grams) was poured into the resulting solution with cooling and stirring. Triethylamine (26.1 ml) was then added subsurface to the cooled solution. After removing insoluble salts by filtration of the resulting reaction mixture, the concentration of the filtrate was increased by removing acetonitrile by simple distillation. The resulting filtrate concentrate was added to 4-methylpiperidinyl pyridine (32 9 grams, 10.187 moles) and the resulting mixture was dissolved in 25 ml of dimethylformamide (DMF) with stirring and heating of the resulting solution to 140° C. Stirring of the solution or reaction mixture was continued at that temperature for 65–70 hours, followed by removing DMF (22 ml recovered) from the resulting dark red reaction mixture by distillation under reduced pressure After cooling the distillation residue or liquor, dichloromethane (75 ml) was added thereto. The resulting organic layer was washed three times with 75 ml of saturated aqueous solution of sodium chloride. The resulting dichloromethane-rich layer was removed, dried over magnesium sulfate and contacted with activated charcoal. Dichloromethane was then removed under reduced pressure (68 ml recovered) The resulting crude product was "recrystallized" from a mixture of 150 ml of ethyl acetate and 50 ml of acetonitrile, yielding a light brown solid product with no defineable crystal structure. The first crop yield was dried under vacuum to provide 15.4 grams of the product The filtrate was concentrated to one third of its original volume, followed by adding 10 ml of ethyl acetate. A second crop of the product precipitated and was collected and dried under vacuum to yield an additional 2.7 grams of product for a combined yield of 18.1 grams. This corresponds to 34.3% yield of the product, which (based on method of preparation) was N-neopentyl-4-(4'-methylpiperidinyl) pyridinium chloride (NPMPPC).

EXAMPLE II

To a one-liter resin kettle equipped with a mechanical stirrer, thermometer and reflux condenser were added 4-chloronitrobenzene (400 grams, 2.54 moles) potassium fluoride (222 1 grams, 3.82 moles) and sulfolane (413.6 grams). (The potassium fluoride used had been dried under vacuum in an oven set at 105° C. and pulverized with a mortar and pestle.) The resulting mixture was heated to 210° C with stirring, followed by adding 2.6 grams of the NPMPPC prepared in Example I, whereupon the resulting reaction mixture turned dark brown. The reaction mixture was stirred at 210° C for a total 9 hours, which period was interrupted after 5 hours by cooling to room temperature (about 20° C) and holding at that temperature overnight, followed by reheating to 210° C. and maintaining that temperature with stirring for the duration of the period. At the end of such period, analysis of a sample of the reaction mixture by high pressure liquid chromatography (HPLC) showed the area of the 4-fluoronitrobenzene (FNB) product peak to be 83.182% and the area of the residual 4-chloronitrobenzene (CNB) peak to be 6.440%, based on the total area of the HPLC curve. The HPLC analysis was made using a Waters Bondapak C18 reverse phase column, a 2-microliter sample loop, a UV detector at 254 nanometers and a dual pump. The solvent system was a 1:1 mixture of the flows from pump A (1:1 methanol:water) and pump B (methanol). The combined flow rate was 1.5 microliters per minute. The peak areas of the resulting FNB (and residual CNB) were measured using a digital integrator. This corresponds to nearly 80 mole percent conversion of the CNB to FNB and at a fast rate.

A total of 287 grams of FNB (80% yield) was recovered in the form of 17 grams of FNB distillate (from an initial 10-plate fractional distillation of a portion of the reaction mixture, which distillation was discontinued in favor of simple distillation) and 270 grams of FNB in the total distillate from the simple distillation.

EXAMPLE III

The procedure of Example I was repeated except that di-n-butylaminopyridine was substituted on an equimolar basis for the 4-methylpiperidinyl pyridine used in Example I. There was obtained N-neopentyl-4-(N',N'-di-n-butylamino)pyridinium chloride (NPDBAPC). (Alternatively, this product can be prepared as described in Example 1 of Brunelle et al., U.S. Pat. No. 4,513,141, which is incorporated herein by reference.)

EXAMPLE IV

A reaction mixture of 85.3 g of 4-chloronitrobenzene (CNB), 45.3 g of potassium fluoride, 1.4 g of the N-neopentyl-4-(N',-N'-di-n-butylamino)pyridinium chloride (NPDBAPC) obtained in Example III in 109.6 g of sulfolane was heated with stirring for 9 hours at 205°–215° C. At the end of this period, HPLC assay of a sample of the reaction mixture indicated less than 1% residual CNB. Simple distillation of the reaction mixture under vacuum gave 73.6 g of 4-fluoronitrobenzene (FNB) for a 96.3% yield.

The mixed salts in the residue from distillation of the reaction mixture were removed by filtration. The resulting filtrate (100 grams) containing sulfolane and NPDBAPC was added with 40 grams of sulfolane which had been used to wash such salts, 134.6 grams of 4-chloronitrobenzene and 74.3 g of potassium fluoride. No additional NPDBAPC was added. HPLC assay indicated 80% FNB and 12.7% residual CNB after heating the resulting reaction mixture with stirring at 210°–215° C. for approximately 13 hours.

EXAMPLE V

A mixture of 4-chloronitrobenzene (CNB, 100 grams, 0.573 mole), potassium fluoride (62 4 grams, 1.07 mole) and NPDBAPC (2 grams, 0.0064 mole) obtained in Example III was heated with stirring at 210°–215° C. for a total of 12 hours. At the end of this period, HPLC assay of a sample of the neat (solventless) reaction mixture indicated 91.388 area percent of 4-fluoronitrobenzene (FNB) and 3.392 area percent of CNB, corresponding to about 90 mole% conversion of CNB 5 to FNB.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. In a process for preparing a fluoroaromatic compound by reaction of a corresponding chloro-aromatic compound with potassium fluoride under halide-exchange conditions in the presence of a catalyzing amount of a phase transfer catalyst, the improvement which comprises using as said catalyst an alkyldiorganopyridinium salt represented by the formula

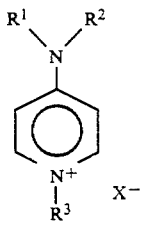

where:
R¹ and R² are monovalent or divalent organo radicals independently selected from substituted and unsubstituted hydrocarbon radicals having from 1 to 13 carbon atoms and divalent alkylene radicals which together can be a part of a cyclic structure forming a ring having from 4 to 8 carbon atoms;
R³ is a monovalent organo radical represented by the formula

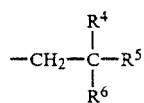

where R⁴, R⁵ and R⁶ are independently selected alkyl radicals having from 1 to 8 carbon atoms, subject to the proviso that the total number of carbon atoms in R³ is not more than about 20; and
X- is an anion selected from the group consisting of fluoride, bromide and chloride, and adding the phase transfer catalyst to the chloro-aromatic compound in one step.

2. The process of claim 1 wherein said salt is N-neopentyl -4-(N',N'-di-n- butylamino)pyridinium chloride.

3. The process of claim 2 wherein said salt is N-neopentyl-4-(N',N'-di-hexylamino)pyridinium chloride.

4. The process of claim 1 wherein said salt is N-neopentyl-4-(4'-methylpiperidinyl)pyridinium chloride.

5. The process of claim 1 wherein said reaction is carried out in an aprotic polar organic solvent.

6. The process of claim 5 wherein said solvent is sulfolane.

7. The process of claim 1 wherein the chloroaromatic compound comprises an aromatic ring, at least one chlorine atom as a substituent on the aromatic ring and at least one activating substituent located in an activating position on the ring for facilitating nucleophilic substitution of fluorine for the chlorine, the activating substituent being an electron-withdrawing agent selected from the group consisting of nitro; cyano; trifluoromethyl; chlorocarbonyl; fluorocarbonyl; phenylcarbonyl wherein the phenyl moiety is unsubstituted or substituted with a substituent other than agents which are at least moderately strong electron-releasing agents; phenylsulfonyl wherein the phenyl moiety is unsubstituted or substituted with a substituent other than agents which are at least moderately strong electron-releasing agents; and a combination of three, four or five additional chlorine atoms.

8. The process of claim 1 wherein the chloroaromatic compound is selected from the group consisting of
(a) 2-chlorobenzonitrile
(b) 4-chlorobenzonitrile
(c) 2-chlorobenzoyl chloride
(d) 4-chlorobenzoyl chloride
(e) 2-chlorobenzoyl fluoride
(f) 4-chlorobenzoyl fluoride
(g) 2-chloro-benzotrifluoride
(h) 4-chloro-benzotrifluoride
(i) tetrachlorobenzene
(j) pentachlorobenzene
(k) hexachlorobenzene
(l) (4,4'-dichloro-)diphenylsulfone
(m) 4,4'-dichlorobenzophenone
(n) 3-chloro-phthalic anhydride
(o) 4-chloro-phthalic anhydride
(p) 3-chloro-phthaloyl dichloride
(q) 4-chloro-phthaloyl dichloride
(r) 1,4-dichloroanthracene-9,10-dione
(s) 3-chloro-4-(trifluoromethyl)pyridine
(t) 3-chloro-4-cyanopyridine
(u) 3-chloro-4-nitropyridine.
(v) 2-chloronitrobenzene
(w) 2,3-dichloronitrobenzene
(x) 4-chloronitrobenzene
(y) 2,4-dichloronitrobenzene and
(z) 2,4,5-trichloronitrobenzene 9. The process of claim 1 wherein the chloroaromatic compound is a chloronitrobenzene.

10. The process of claim 1 wherein the chloroaromatic compound is a melt and said reaction is carried out as a neat reaction.

11. The process of claim 10 wherein said chloroaromatic compound is a chloronitrobenzene compound.

* * * * *